United States Patent [19]

Rosenblum

[11] 4,307,609

[45] Dec. 29, 1981

[54] LIQUID DENSITY METER

[75] Inventor: Frank Rosenblum, Ville St. Laurent, Canada

[73] Assignee: Noranda Mines Limited, Toronto, Canada

[21] Appl. No.: 125,920

[22] Filed: Feb. 29, 1980

[30] Foreign Application Priority Data

Nov. 29, 1979 [CA] Canada .................................. 340920

[51] Int. Cl.³ .............................................. G01N 9/26
[52] U.S. Cl. ......................................... 73/438; 73/439
[58] Field of Search .................. 73/438, 439, 299, 716

[56] References Cited

U.S. PATENT DOCUMENTS

| | | | |
|---|---|---|---|
| 3,397,581 | 8/1968 | Bush | 73/716 |
| 4,116,076 | 9/1978 | Nolte | 73/299 |
| 4,136,567 | 1/1979 | Rosenblum | 73/438 |

FOREIGN PATENT DOCUMENTS 436996  12/1974  U.S.S.R. ................................. 73/438

Primary Examiner—James J. Gill
Attorney, Agent, or Firm—Fleit & Jacobson

[57] ABSTRACT

An apparatus for measuring the density of a liquid or of a suspension of solids in a liquid is disclosed. The apparatus comprises two pressure sensors adapted to be mounted in the liquid so that the two sensors are vertically at predetermined levels apart, a differential pressure transducer, and proper tubings including a differential pressure zeroing device interconnecting the pressure sensors to the differential pressure transducer, for providing an output proportional to the density of the liquid which is compensated for the differential pressure caused by the differential height of said pressure sensors in the liquid. In a preferred embodiment of the invention, the differential pressure zeroing device is a pair of U-tubes filled with liquid and the tubings comprise gas filled tubings interconnecting one branch of each U-tube to respective pressure sensors and the other branch of each U-tube to the differential pressure transducer.

8 Claims, 7 Drawing Figures

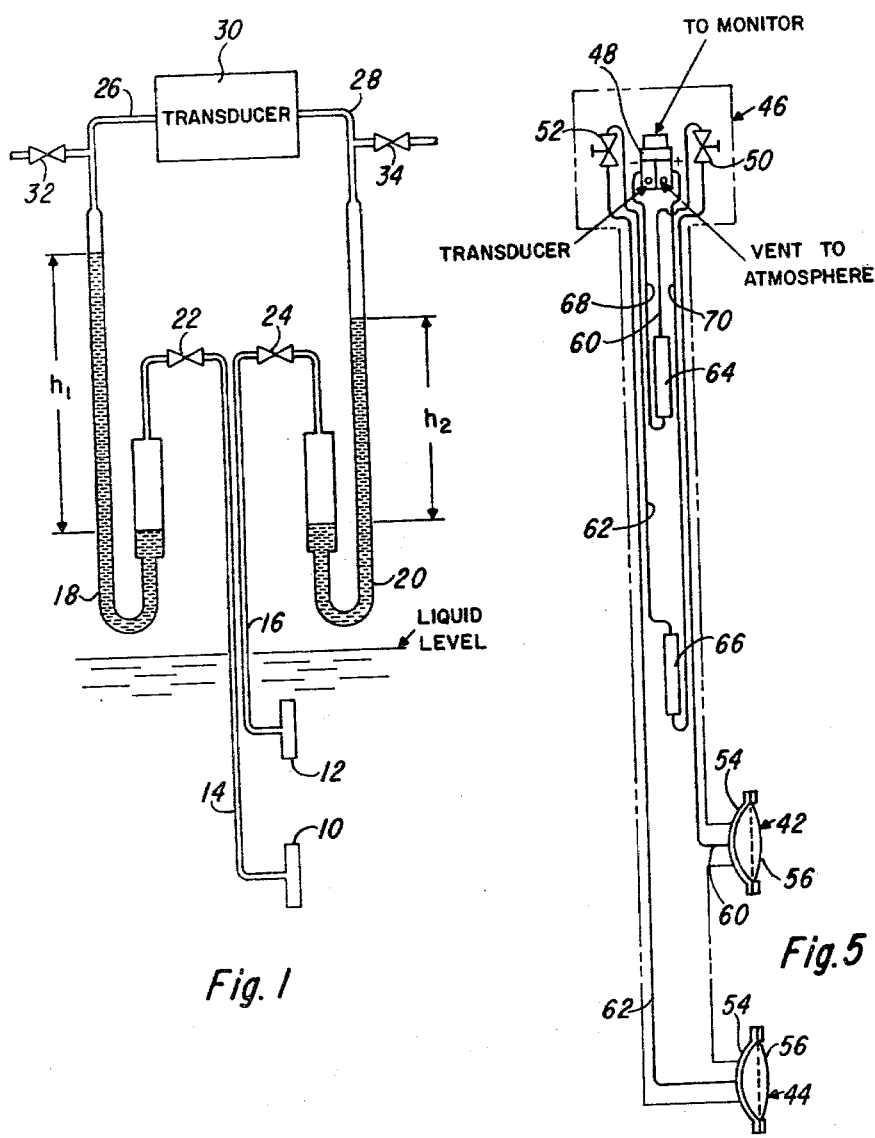

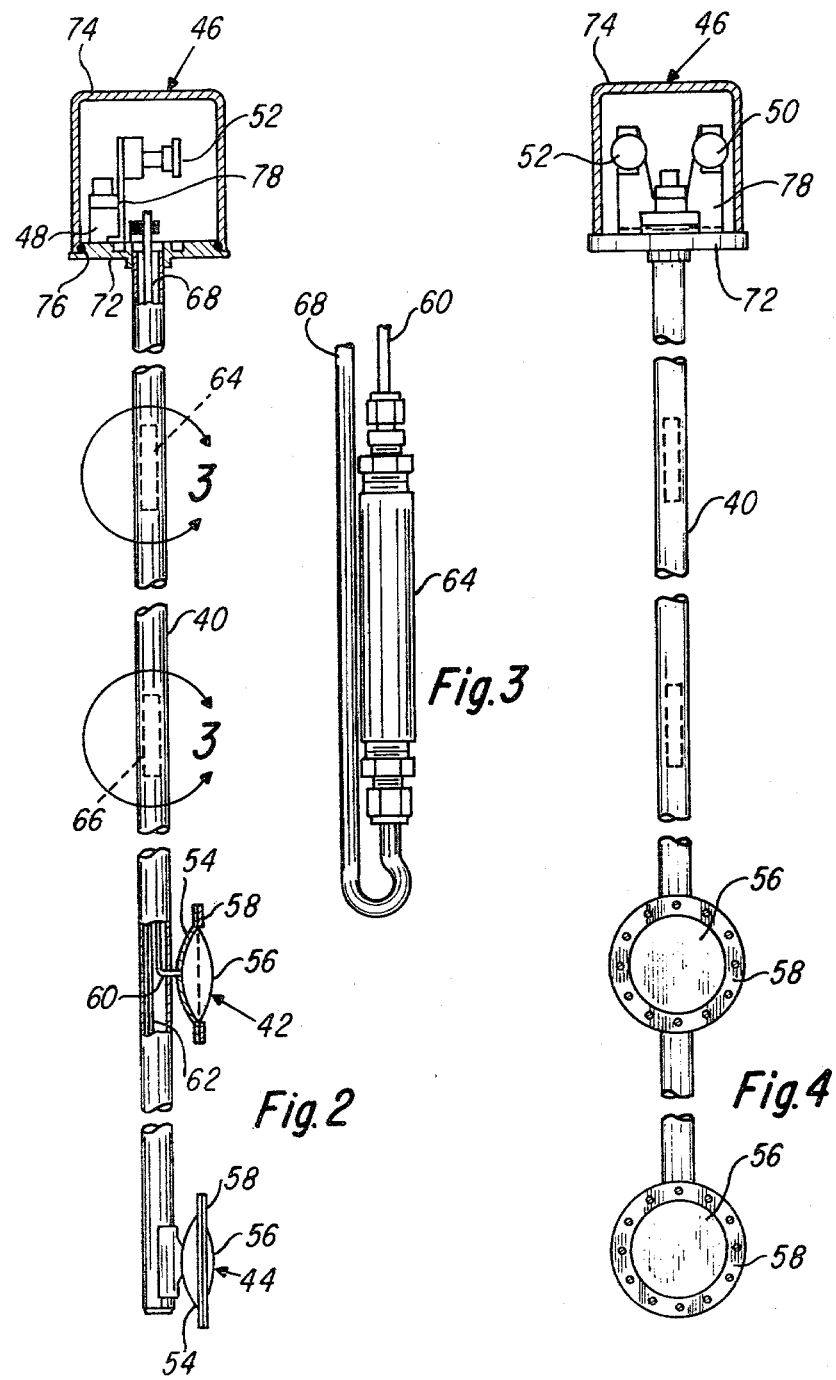

LIQUID DENSITY METER

This invention relates to an apparatus for measuring the density of a liquid or of a suspension of solids in a liquid, and more particularly to an apparatus for providing an accurate and reliable electrical output which is proportional to the density of the liquid being measured.

The apparatus is based on the use of two vertically separated pressure sensors connected by proper means to a differential pressure transducer. The use of a transducer connected directly across pressure sensors to provide an electrical output proportional to the density of a test liquid is well known. An apparatus of this type is disclosed in applicant's U.S. Pat. No. 4,136,567 issued Jan. 30, 1979. However, the sensitivity of such an apparatus is limited. For example, when two sensors 14 inches apart are immersed in water, the pressure across the transducer is about 0.5 psi. When the same sensors are immersed in a solution having a density of 1.1 g/L the differential pressure across the transducer is now about 0.55 psi. Thus, a change in density of 0.1 unit results in a 0.05 psi change in pressure. For a probe to have a full-scale sensitivity of 0.1 g/L a differential pressure transducer of range 0.05 psi would therefore be required to give optimum performance. However, the above example shows that a far less sensitive transducer of range at least 0.55 psi must be used because of the initial 0.5 psi load exerted on it when the pressure sensors are immersed in water. Less than 10% of the transducer's range is therefore used to provide the full-scale output. It is obvious that such an apparatus will produce more noise and less stability than an equivalent system where the full range of a transducer can be used.

It is therefore the object of the present invention to provide a liquid density meter wherein the pressure range of the meter is matched to the full range of the transducer.

It is a further object of the present invention to provide a liquid density meter having a high resolution and low drift output such that a small change in density of a test liquid of say 0.001 g/L is transformed into a meaningful change in output voltage.

The apparatus, in accordance with the invention, comprises two pressure sensors adapted to be mounted in the liquid to be tested so that the two sensors are vertically at predetermined levels apart, a differential pressure transducer, and tubings including a differential pressure zeroing device interconnecting the pressure sensors to the differential pressure transducers, for providing an output proportional to the density of the liquid which is compensated for the differential pressure caused by the differential height of the pressure sensors in the liquid.

In a preferred embodiment of the invention, the differential pressure zeroing device comprises a pair of U-tubes filled with liquid, and the tubings comprise gas filled tubings interconnecting one branch of each U-tube to a respective pressure sensor and the other branch of each U-tube to the differential pressure transducer.

In a still more preferred embodiment of the invention, the two pressure sensors are mounted at one end of a holder of predetermined length and the differential pressure sensor at the other end of the holder. The holder is hollow and the tubings extend through the center of the holder. The U-tubes are also located one above the other within the hollow holder.

The invention will now be disclosed, by way of example, with reference to preferred embodiments in which:

FIG. 1 illustrates a schematic view of a liquid density meter in accordance with the invention;

FIGS. 2 and 4 illustrate side and front views of another embodiment of a liquid density meter in accordance with the invention which is portable;

FIG. 3 illustrates an enlarged view of a portion of the embodiment within the line 3—3 of FIG. 2;

FIG. 5 illustrates a schematic diagram of the embodiment illustrated in FIGS. 2–4;

Figure 6:
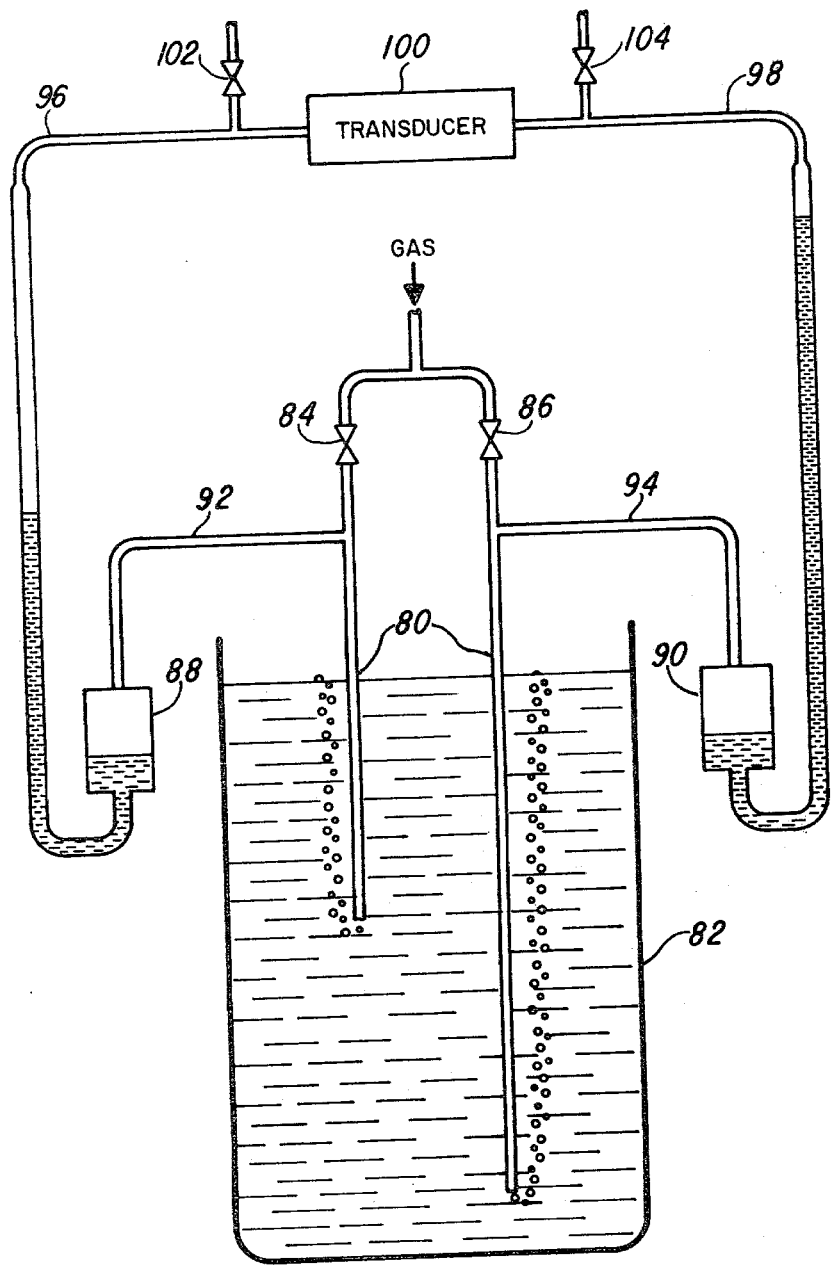
FIG. 6 illustrates another embodiment of the invention.

Referring to FIG. 1, there is shown an apparatus for measuring the density of a liquid comprising two vertically spaced sensors 10 and 12 adapted to be immersed in a body of liquid and each coupled by means of gas filled tubings 14 and 16, respectively, to separate liquid filled U-tubes 18 and 20 through valves 22 and 24. The other branch of each U-tube is in turn connected by means of gas filled tubings 26 and 28 to a differential pressure transducer 30. Valves 32 and 34 are located in tubings 26 and 28 to permit opening of these tubings to the atmosphere.

With all valves 22, 24, 32 and 34 opened, the liquid density meter is first immersed in the body of liquid. The liquid level in the two U-tubes 18 and 20 will rise to heights $h_1$ and $h_2$, respectively. Since valves 32 and 34 are open, the pressure in tubings 26 and 28 and the top of the U-tubes remains atmospheric. Valves 32 and 34 are then closed and the liquid density meter is lowered deeper into the liquid. The liquid levels in the U-tubes will rise slightly, applying an equal positive pressure on both sides of the transducer, still leaving the differential pressure applied to the transducer unchanged. In effect, the two U-tubes act as a pressure zeroing device. A subsequent change in density of the liquid will be detected by the differential pressure transducer. It will be noted, however, that the base line is zero, and that this will allow the use of the full span of the transducer for the variations in density. For example, using two pressure sensors 28 inches apart, a differential pressure transducer of range 0–0.1 psi could be used for a density meter which can monitor a solution density variation of 0.1 g/L full scale, whereas a differential pressure transducer of range at least 0–1.1 psi was previously needed as it was necessary to provide for the reading of the 1.0 psi caused by the differential height of 28 inches of water between the two pressure sensors.

FIGS. 2–4 of the drawings illustrate an embodiment of a portable liquid density meter comprising a holder 40, two pressure sensors 42 and 44 mounted a predetermined distance apart at one end of the holder and an enclosure 46 at the other end of the holder for housing a differential pressure transducer 48 and two valves 50 and 52. The holder and the pressure sensors are preferably made of stainless steel or other corrosion and abrasion resistant material so as to permit the use of the density measuring device in corrosive and abrasive solutions. The two pressure sensors each consist of a shallow housing 54 which is closed by a diaphragm 56 itself secured to the housing by an annular ring 58. The housings of the pressure sensors 42 and 44 have a hole at the bottom to which is welded the end of tubings 60 and 62, respectively, which extend through the center of the holder up to the enclosure 46, through respective valves 50 and 52, and down into the holder to the top of respective liquid reservoirs 64 and 66, each forming one branch of a U-tube. The bottoms of the liquid reservoirs 64 and 66 are connected to the differential pressure transducer through tubings 68 and 70, respectively, which also extend through the center of the hollow holder 40 and form the second branch of the U-tubes.

The enclosure 46 consists of a bottom plate 72 which is secured to the end of the holder 40 and of an inverted cup housing 74 which is secured to the bottom plate. An O-ring 76 is placed in an annular slot in the bottom plate for sealing enclosure 46 to bottom plate 72. This permits the use of the density mesuring devices in adverse working conditions. A bracket 78 is secured to the bottom plate 72 for mounting the differential pressure transducer 48 and the valves 50 and 52.

FIG. 5 of the drawings illustrates schematically the various tubings interconnecting the pressure sensors to the U-tubes and the U-tubes to the differential pressure transducer. It will be noted that the transducer has integral vents to the atmosphere thus eliminating the use of separate valves (valves 32 and 34 in FIG. 1) in the tubings 68 and 70. The top of the transducer has an output (not shown) adapted for connection to a suitable monitor.

The above disclosed portable density measuring device operates in the same mannerr as the one disclosed in FIG. 1. Valves 22 and 24 in the embodiment of FIG. 1 and 50 and 52 in the embodiment of FIGS. 3-5 are preferably closed when the apparatus is removed from a body of liquid so as to prevent damage to the transducer due to the sudden differential pressure which is applied to the transducer when the pressure sensors are removed from the liquid. Valves 22 and 24 are also closed during calibration of the density meter by immersion of the density meter into successive solutions of known densities.

FIG. 6 illustrates another embodiment of the invention wherein two tubes 80 are immersed into a liquid reservoir 82. The tubes are connected to a source of gas pressure and the amount of gas fed into each tube is controlled by valves 84 and 86 such that gas bubbles are merely forming into the liquid. The back pressure created in each tube is applied to separate liquid filled U-tubes 88 and 90 through tubings 92 and 94 connected to respective tubes 80. The other branch of each U-tube is in turn connected by means of tubings 96 and 98 to a differential pressure transducer 100. Valves 102 and 104 are located in tubings 96 and 98 to permit opening of these tubings to the atmosphere. This embodiment is equivalent to and operates in the same manner as the one disclosed in FIG. 1, except that the type of pressure sensors used is different. This embodiment could also be made portable as in the embodiment of FIGS. 2-5 by passing tubes 80 inside a hollow holder and out through two openings spaced apart a predetermined distance at the lower end of the holder. The U-tubes could be placed inside the holder as in the embodiment of FIGS. 2-5 together with the tubings 96 and 98 extending to the transducer 100. Finally, the tranducers, the valves and the gas inlet could be placed in a housing at the upper end of the holder.

Figure 7:
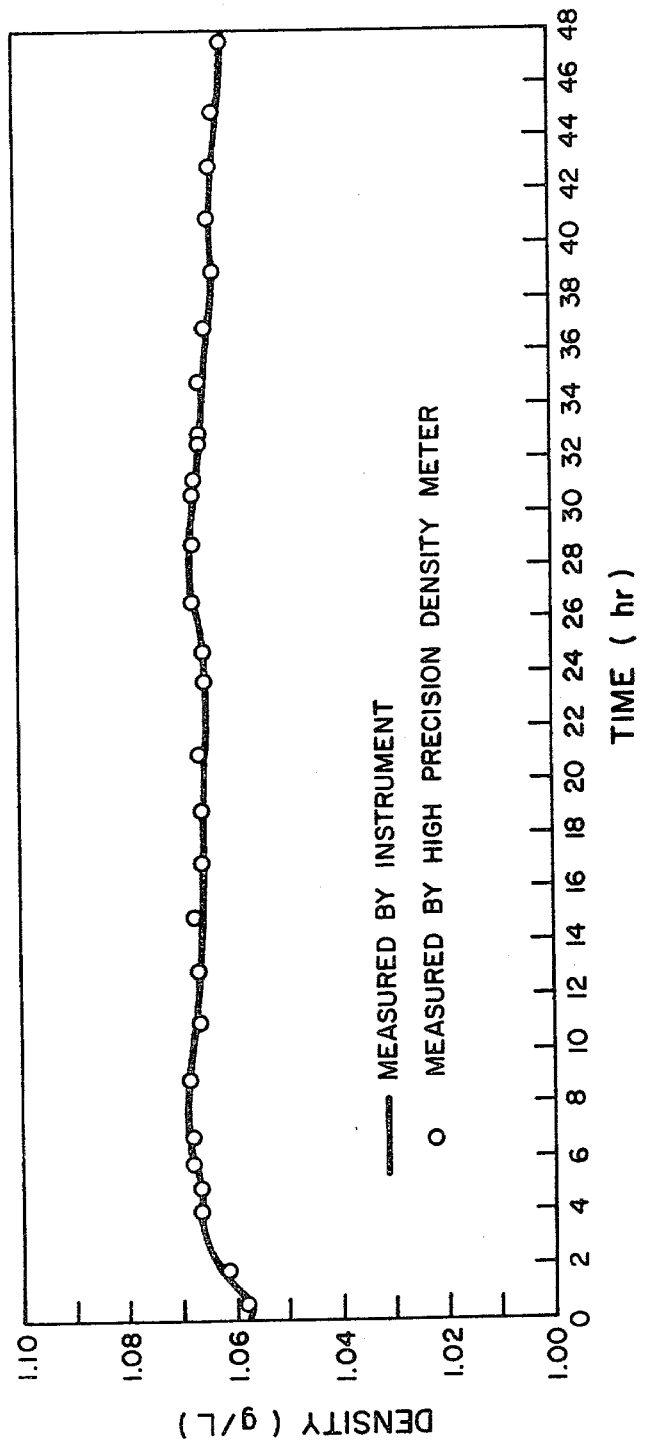
FIG. 7 illustrates a plot versus time of the density of the liquid in a holding tank, as measured with an apparatus in accordance with the invention, and with a commercial high precision liquid density measuring instrument.

The liquid density meter in accordance with the invention was tested in a CuSO4 holding tank at Noranda Mines Limited (Division Matagami). A record of the density meter output for the test over a period of 48 hours is shown in FIG. 7. The density was checked regularly with a commercial liquid density meter having a precision of 0.0005 g/L. The readings of the commercial instrument are shown by small circles in FIG. 7. It is clearly seen that the output of the liquid density meter in accordance with the invention compares very advantageously with that of the precise commercial instrument.

Although the invention has been disclosed with reference to preferred embodiments, it is to be understood that other alternatives are also envisaged and that the invention is not limited to such embodiments.

The embodiments of the invention in which an exclusive property or privilege is claimed are defined as follows:

1. An apparatus for measuring the density of a liquid or of a suspension of solids in a liquid comprising:
   (a) two pressure sensors adapted to be mounted in the liquid so that the two sensors are vertically at predetermined levels apart;
   (b) a differential pressure transducer; and
   (c) a differential pressure zeroing device interconnecting said pressure sensors to said differential pressure transducer, for providing an output proportional to the density of the liquid which is compensated for the differential pressure caused by the differential height of said pressure sensors in the liquid, said differential pressure zeroing device comprising a pair of U-tubes filled with liquid, first gas filled tubings interconnecting one branch of each U-tube to a respective pressure sensor, second fluid filled tubings interconnecting the other branch of each U-tube to said differential pressure transducer, and equalizing means for equalizing the pressure applied to each side of the differential pressure transducer when the apparatus is immersed into a liquid of standard density.

2. An apparatus as defined in claim 1, wherein the two pressure sensors are mounted at one end of a holder of predetermined length and the differential pressure transducer at the other end of the holder.

3. An apparatus as defined in claim 2, wherein the holder is hollow, and wherein said tubings extend through the center of said holder.

4. An apparatus as defined in claim 3, wherein said U-tubes are also located within said hollow holder.

5. An apparatus as defined in claim 2, further comprising a valve located in each tubing interconnecting said U-tubes to the pressure sensors and adapted to be opened when the apparatus is immersed into the liquid and closed when the apparatus is removed from the liquid.

6. An apparatus as defined in claim 1, wherein said equalizing means comprises a valve communicating said second fluid filled tubings with the atmosphere and adapted to be opened when the apparatus is immersed into the liquid for bleeding the fluid in said tubings, and to be closed after the apparatus is immersed into the liquid.

7. An apparatus as defined in claim 1, wherein said pressure sensors are diaphragm type pressure sensors.

8. An apparatus as defined in claim 1, wherein the pressure sensors are two tubes extending into the liquid so that the lower ends thereof are at said predetermined levels apart and means for feeding gas into each of said tubings at a pressure such that bubbles are just beginning to form into the liquid, and wherein the back pressure thus created is applied to said differential pressure transducer.

* * * * *